(12) United States Patent
Clark et al.

(10) Patent No.: US 9,399,009 B1
(45) Date of Patent: Jul. 26, 2016

(54) COMPOSITION AND METHOD OF TREATING SKIN CONDITIONS

(71) Applicant: Clark Pharmaceuticals LLC, Fort Worth, TX (US)

(72) Inventors: Stephen W. Clark, Fort Worth, TX (US); Natalie Barger, Fort Worth, TX (US)

(73) Assignee: CLARK PHARMACEUTICALS, LLC, Fort Worth, TX (US)

( * ) Notice: Subject to any disclaimer, the term of this patent is extended or adjusted under 35 U.S.C. 154(b) by 0 days.

(21) Appl. No.: 14/632,149

(22) Filed: Feb. 26, 2015

Related U.S. Application Data

(63) Continuation of application No. 14/040,266, filed on Sep. 27, 2013, now abandoned.

(60) Provisional application No. 61/744,925, filed on Oct. 5, 2012.

(51) Int. Cl.
| | | |
|---|---|---|
| *A01N 43/00* | (2006.01) | |
| *A61K 8/60* | (2006.01) | |
| *A61Q 19/00* | (2006.01) | |
| *A61K 8/368* | (2006.01) | |
| *A61K 8/365* | (2006.01) | |
| *A61K 8/42* | (2006.01) | |
| *A61K 8/49* | (2006.01) | |
| *A61K 8/34* | (2006.01) | |

(52) U.S. Cl.
CPC ... *A61K 8/60* (2013.01); *A61K 8/34* (2013.01); *A61K 8/365* (2013.01); *A61K 8/368* (2013.01); *A61K 8/42* (2013.01); *A61K 8/4926* (2013.01); *A61K 8/4973* (2013.01); *A61Q 19/007* (2013.01); *A61K 2800/5922* (2013.01)

(58) Field of Classification Search
None
See application file for complete search history.

(56) References Cited

U.S. PATENT DOCUMENTS

| 8,003,594 B2 * | 8/2011 | Cunningham | A61K 8/046 222/190 |
|---|---|---|---|
| 2008/0069779 A1 * | 3/2008 | Tamarkin | A61K 8/046 424/45 |

OTHER PUBLICATIONS

Prance (Cosmetics, Symraise receives industry recognition for ingredient innovation, 2007, http://www.cosmeticsdesign-europe.com/content/view/print/12152).*
Inspired by Nature (Cosmetics design-eurpoe.com, Jun. 20, 2011).

* cited by examiner

*Primary Examiner* — Dennis Heyer
*Assistant Examiner* — Daniel M Podgorski
(74) *Attorney, Agent, or Firm* — Martin G. Ozinga; Phillips Murrah PC

(57) ABSTRACT

The present invention is a composition and method of treatment for skin disorders, conditions, and severe skin dryness in general through topical systematic and periodic application of a formulation that generally may include salicylic acid, glycolic acid, urea, dimethyl isosorbide, ethoxydiglycol, barrier repair agents, anti-irritants, humectants, and also has an acidic pH formulation.

1 Claim, No Drawings

COMPOSITION AND METHOD OF TREATING SKIN CONDITIONS

CROSS-REFERENCE TO RELATED APPLICATIONS

Priority is claimed from provisional patent application U.S. Ser. No. 61/744,925 filed on Oct. 5, 2012 and incorporated by reference herein.

BACKGROUND OF THE INVENTION

1. Field of the Invention

In general, the present invention is a composition and method of treatment for skin disorders, conditions, and severe skin dryness in general such as but not limited to hyperkeratosis and or severe dry skin conditions that may include xerosis, ichthyosis, atopic dermatitis, pruritus, eczema, and asteatosis. More in particular, the present invention is a systematic and periodic application of a topical formulation that may include salicylic acid, glycolic acid, urea, dimethyl isosorbide, ethoxydiglycol, barrier repair agents, anti-irritants, and humectants. To optimize the delivery and efficacy of these agents, the pH of the formulation may be acidic.

2. Description of the Prior Art

Skin care is a large and ever increasing concern. Although anyone can develop severe dry skin and associated disorders, dry skin is more likely to occur in older adults, people living in dry, cold, or low-humidity climates, and people who bathe or shower frequently. Skin problems may be caused by various factors such as numerous environmental factors, genetics and age related factors as discussed further below. Of note, the US total skin care market was estimated at $8.3 billion in 2008, up 1.1% over 2007. From 2003 to 2008, the market for premium skin care products grew 18% or a compounded annual growth rate of 3.4%. Contributing to this growth was the anti-aging segment, which grew 58.8% over this same time frame to approximately $2.5 billion. Needless to say, medical professionals as well as consumers are constantly looking for new and improved treatments that provide solutions and preventative care to improve health needs associated with skin issues and skin care in general.

Generally, itchy, dry skin is caused by environmental factors, such as cold weather, frequent bathing, and by medical conditions, such as atopic dermatitis and malnutrition. Dry skin develops due to a decrease in the natural oils in the outer layer of skin, which makes the skin lose water. Ordinarily, dry skin is not serious, but it can be uncomfortable and unsightly, turning plump cells into shriveled ones and creating lines and wrinkles.

Serious dry skin conditions, an inherited group of disorders called ichthyosis, can sometimes be disfiguring, causing psychological distress. Fortunately, most dry skin results from environmental factors that can be wholly or partially controlled. These include exposure to hot or cold weather with low humidity levels and excessive bathing.

Chronic or severe dry skin problems normally require a dermatologist's evaluation. Dry skin is more prevalent in winter, but can be a problem for patients year-round. And, although skin is often driest on the arms and lower legs, this pattern can vary considerably from person to person. Furthermore, signs and symptoms of dry skin depend on age, health status, locale, and the amount of time spent outdoors.

Symptoms of dry skin include a feeling of skin tightness, especially after showering, bathing or swimming; skin that appears shrunken or dehydrated; skin that feels and looks rough rather than smooth; itching, also known as pruritus, that sometimes may be intense; slight to severe flaking, scaling or peeling; fine lines or cracks; redness; and deep fissures that may bleed. Though most cases of dry skin, also known as xerosis, are caused by environmental exposures, certain diseases also can significantly alter the function and appearance of the skin, especially in patients over the age of 50.

Causes of dry skin may include weather where, in general, skin is driest in winter, when temperatures and humidity levels plummet. Winter conditions also tend to make many existing skin conditions worse. However, the reverse may be true for people living in desert regions, where temperatures can soar, but humidity levels remain low.

Other causes of dry skin may be central heating and air conditioning as well as wood-burning stoves, space heaters, and fireplaces all reduce humidity and dry the skin. Also, frequent showering or bathing, especially if the baths are hot and long, breaks down the lipid barriers in skin. So does frequent swimming, particularly in heavily chlorinated pools. Still further, many popular soaps and detergents strip lipids and water from the skin especially harsh soaps and detergents. Deodorant and antibacterial soaps are usually the most damaging, as are many shampoos that dry out the scalp.

Still other causes may me be sun exposure. Like all types of heat, the sun dries the skin and damage from ultraviolet radiation penetrates far beyond the top layer of skin also known as the epidermis. The most significant damage occurs deep in the dermis, where collagen and elastin fibers break down much more quickly than they should, leading to deep wrinkles and loose, sagging skin also known as solar elastosis. Sun damaged skin may have the appearance of dry skin.

Furthermore, one of the more common types of eczema, atopic dermatitis, and those affected have more sensitive and drier skin. Many persons with mild eczema confuse this skin condition with excessive dryness. Areas commonly affected include the face, sides of the neck, and fold areas around the elbows, wrists, knees and ankles. Another cause may be psoriasis. This skin condition is marked by a rapid buildup of rough, dry, dead skin cells that form thick scales. And still further, thyroid disorders, also known as hypothyroidism, can create a condition that occurs when the thyroid produces too little thyroid hormones, which reduces the activity of the sweat and oil glands and leads to rough dry skin.

Still further, some people have a tendency toward eczema, also known as atopic dermatitis, wherein dry skin that's not cared for can lead toward an actual case of actual eczema. This excessive dryness can lead to activation of the disease, causing redness, cracking and inflammation. Those with the tendency may also be more likely to have inflammation of the hair follicles, also known as folliculitis. Also, people with a tendency toward eczema may develop cellulitis, which can be a potentially serious bacterial infection of the skin's underlying tissues that in turn can cause bacteria to enter the lymphatic system and blood vessels. These complications are most likely to occur when the skin's normal protective mechanisms are severely compromised. And as referred to previously, severely dry skin can cause deep cracks or fissures, which can open up and bleed, providing an avenue for invading bacteria.

Although anyone can develop severe dry skin, dry skin is more likely to occur in older adults. Mature skin is also often prone to dryness due to deficiencies in skin barrier integrity, decline in sebaceous and sweat gland activity, decreased blood flow, and loss of connective tissue. Specifically, mature skin is marked by decreased synthesis of skin barrier lipids, reduced cohesiveness of superficial skin cells, reduction of collagen fibers, and a steady natural decrease in the skin's natural water content. Each of these aspects impacts the skin's ability to retain moisture. Additional side effects due to dehydration involve skin tears, allergic reaction, infection, prolonged healing time due to depressed immune response, and itch.

Also of note, mature skin is often prone to hyperkeratotic conditions due to depressed cell renewal. Hyperkeratosis is generally the thickening of the stratum corneum, often associated with a qualitative abnormality of the keratin, and usually accompanied by an increase in the granular layer. As the corneum layer normally varies greatly in thickness in different sites, some experience is needed to assess minor degrees of hyperkeratosis. It can be caused by vitamin A deficiency or chronic exposure to arsenic. Knees and elbows are typical sites of HP, whereas Keratosis Pilaris (KP) usually affects the back of the arms and front of the legs. Follicular hyperkeratosis dass, also called phrynoderma, is a skin condition characterized by excessive development of keratin in hair follicles, resulting in rough, cone-shaped, elevated papules. The openings are often closed with a white plug of encrusted sebum. Plantar hyperkeratosis is hyperkeratosis of the sole of the foot.

The above discussed limitations in the prior art is not exhaustive. It is therefore desirable to provide a new and improved treatment for skin disorders, conditions, and severe skin dryness in general such as but not limited to hyperkeratosis and or severe dry skin conditions that may include xerosis, ichthyosis, atopic dermatitis, pruritus, eczema, and asteatosis. The current invention provides an inexpensive and effective composition and method of treatment for skin disorders, conditions and severe skin dryness not currently found in the known art.

SUMMARY OF THE INVENTION

In view of the foregoing disadvantages inherent in the known types of compositions and methods of treating skin disorders as well as dry skin in general now present in the prior art, the present invention provides a new and improved effective composition and method of using the same where the prior art fails. As such, the general purpose of the present invention, which will be described subsequently in greater detail, is to provide a new and improved composition and method for the treatment which has all the advantages of the prior art and none of the disadvantages.

To attain this, the present invention essentially comprises a systematic and periodic application of a topical non-toxic formulation that may include salicylic acid, glycolic acid, urea, dimethyl isosorbide, ethoxydiglycol, barrier repair agents, anti-irritants, and humectants. The current invention contemplates the formulation may be utilized in a lotion, cream, liquid, and or combinations thereof and provide an advanced and unique approach to the overall treatment and management of hyperkeratotic conditions, severe dry skin, ichthyosis, and KP. The invention will deliver an effective keratolytic effect, clear blockages, remove dead skin cells, and rid the skin of other cellular debris. The pH of the formulation will be acidic to maintain the acids in their "active" form and a penetration enhancer, dimethyl isosorbide, may be utilized.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction, arrangement of the components, and amounts thereof set forth in the following description. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other compositions, methods, and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide a new and improved composition and method of treating skin disorders and skin dryness in general that may be easily and effectively used by those afflicted for sufferers of severe dry skin and hyperkeratotic conditions. In addition, the current invention will be effective in treating patients with xerosis, ichthyosis, atopic dermatitis, eczema, and asteatosis.

It is a further object of the present invention to provide a new and improved composition and method of treating skin disorders and skin dryness in general that may be an essential element in an ideal treatment regimen for severe dry skin conditions in mature skin.

An even further object of the present invention is to provide a new and improved composition and method of treating skin disorders and skin dryness that is susceptible to a low cost of manufacture with regard to ingredients and associated labor of producing same, and, thus accordingly, is then susceptible to low prices of sale to the consuming public thereby making such economically available.

Still another object of the present invention is to provide a new and improved composition and method of treating skin disorders and skin dryness which provides all of the advantages of the prior art, while simultaneously overcoming some of the disadvantages normally associated therewith.

Another object of the present invention is to provide a new and improved composition and method of treating skin disorders and skin dryness that may be used over large areas of skin for those afflicted without or with reduced detrimental side effects.

Yet another object of the present invention is to provide a new and improved composition and method of treating skin disorders and skin dryness that is commercially available such that public awareness is garnered and those afflicted will have a viable and readily available treatment.

An even further object of the present invention is to provide a new and improved composition and method of treating skin disorders and skin dryness in general that combines proven ingredients that have already passed F.D.A. approval.

Still another object of the present invention is to provide a new and improved composition and method of treating skin disorders and skin dryness that may be utilized in a cream and or lotion that is non-irritating, fragrance free, and contains no known sensitizing ingredients and provides a silky smooth feel allowing for easy application and quick absorption. These, together with other objects of the invention, along with the various features of novelty, which characterize the invention, are pointed out with particularity in the claims annexed to and forming a part of this disclosure. For a better understanding of the invention, its operating advantages, and the specific objects attained by its uses, reference should be had to the accompanying descriptive matter in which there are illustrated preferred embodiments of the invention.

DETAILED DESCRIPTION

In a preferred embodiment, the composition generally comprises a composition and method of treatment for skin disorders and skin dryness through topical systematic and periodic application of a formulation. The formulation may be utilized as a cream, lotion, liquid, and combinations thereof. It is also understood that the following description of said components is not limited to exact percentages, quantities, or ingredients and that it is understood equivalent ingredients known in the art may be substituted or added. Due to the nature of skin disorders and skin dryness, a preferred embodiment of the invention provides a treatment that will generally penetrate and stay on the top two layers of skin.

A Preferred Embodiment

AHAs (alpha hydroxyl acids) promote cell renewal by weakening the bonds between neighboring skin cells, thus allowing them to be more easily shed. Unfortunately, keratolytic agents degrade keratin fibers that can accumulate and clog follicles. Utilizing a combination of Salicylic Acid, Glycolic Acid, and Urea will deliver an effective keratolytic effect, clear blockages, remove dead skin cells, and rid the skin of other cellular debris. To optimize the delivery and efficacy of these agents, the pH of the formulation will be acidic (to maintain the acids in their "active" form) and a penetration enhancer, Dimethyl Isosorbide, will be added. Lastly, the formulation will be rounded out by addition of barrier repair agents, anti-irritants, and humectants.

In addition, the non-comedogenic emollients and humectants in a preferred embodiment of the invention bind moisture to the skin to provide long-lasting moisturization; free of fragrances, parabens, lanolin, and mineral oil. Helps restore and maintain the skin's natural protective barrier. A preferred embodiment of the invention provides a cream and or lotion that spreads easily and smoothly, absorbs rapidly, and never feels greasy. The invention may provide all-day moisturization with a single application and is clinically proven to increase skin hydration. It contains SKINMIMICS, a multi-lamellar concentrate of long chain ceramides, cholesterol, behenic acid, and sphingosine that demonstrates a reparative effect on the stratum corneum. Not only do its components reconstitute the skin barrier, but they also help to stimulate lipid synthesis and epidermal renewal. SKINMIMICS is designed for mature skin to help revitalize water management in the epidermisceramides, naturally occurring components of the skin that play a key role in enhancing and restoring the skin's protective function. It is contemplated the current invention may be part of a daily skin care routine specifically formulated for mature skin.

The current invention contemplates a formulation as follows in TABLE 1. It is understood the current invention is not limited to same and the below is for illustrative purposes.

TABLE 1

| TRADE NAME | INCI NAME | CONCEN-TRATION (W/W) | FUNCTION |
|---|---|---|---|
| Miscellaneous | | QS to 100% | Purified water, thickener, emollients, preservative, fragrance, pH adjuster, etc. |
| Transcutol P | Ethoxydiglycol | 3% | Penetration enhancer; optimizes the delivery of skin care actives; |
| Polypore 450 SA | Allyl Methacrylates Crosspolymer (and) Salicylic Acid | 0.9% (0.45% Sal Acid) | BHA; Keratolytic agent; delivery system helps to mitigate irritation |
| Urea | Urea | 5% | Keratolytic and moisturizing agent |
| Glycolic Acid | Glycolic Acid | 10% | AHA to promote cell turnover and renewal |
| Symrepair | Hexyldecanol (and) Bisabolol (and) Cetyl Hydroxyproline Palmitate (and) Stearic Acid (and) *Brassica Campestris* (Rapeseed) Sterols | 3% | Barrier repair and anti-inflammatory |
| Generol 122 N PRL | *Glycine Soja* (Soybean) Sterols | 0.75% | Barrier repair, anti-inflammatory, and improvements in skin elasticity |
| Pentavitin | Saccharide Isomerate | 4% | Humectant; substantive and durable hydrating effect; effective in low humidity environments; combats the drying effects of AHAs |
| SymCalmin | Butylene Glycol (and) Pentylene Glycol (and) Hydroxyphenyl Propamidobenzoic Acid | 2% | Anti-itch and anti-redness |
| Niacinamide | Niacinamide | 0.5% | Anti-oxidant anti-inflammatory, and barrier repair |

In another preferred embodiment, the current invention contemplates a formulation as follows in TABLE 2. It is understood the current invention is not limited to same and the below is for illustrative purposes.

TABLE 2

| CTFA Name | Trade Name | % (w/w) |
|---|---|---|
| Purified Water | Purified Water | 38.250 |
| Disodium EDTA | Versene NA | 0.100 |
| Niacinamide | Niacinamide | 0.500 |
| Urea | Urea | 5.000 |
| Xanthan Gum (and) *Acacia Senegal* Gum | Solagum AX | 1.000 |
| Glycerin USP | Glycerin | 1.000 |
| Ethoxydiglycol | Transcutol CG | 3.000 |
| Propylene Glycol | Propylene Glycol | 2.000 |
| Salicylic Acid (and) Allyl Methacrylates Copolymer | Polypore 450 SA | 0.900 |
| Glycolic Acid (and) Ammonium Glycolate | Glycolic 3.8 | 18.500 |
| Cetearyl Alcohol (and) Dicetyl Phosphate (and) Ceteth-10 Phosphate | Crodafos CES | 2.000 |
| PEG-100 Stearate (and) Glyceryl Stearate | Arlacel 165 | 3.000 |
| Caprylic/Capric Triglycerides | Neobee M5 | 5.000 |
| *Glycine Soja* (Soybean) Sterols | Generol 122 N PRL | 0.250 |
| Stearyl Alcohol | Stearyl Alcohol | 2.000 |

TABLE 2-continued

| CTFA Name | Trade Name | % (w/w) |
|---|---|---|
| Dimethicone | DC 200, 350cst | 3.000 |
| Ceramide NP (and) Ceramide AP (and) Ceramide EOP (and) Phytosphingosine (and) Cholesterol (and) Sodium Lauroyl Lactylate (and) Carbomer (and) Xanthan Gum | SK Influx | 2.000 |
| Saccharide Isomerate | Pentavitin | 4.000 |
| Water (and) Glycerin (and) *Avena Sativa* (Oat) Kernel Extract | DragoCalm | 2.000 |
| Phenoxyethanol (and) Ethylhexylglycerin | Euxyl PE 9010 | 1.000 |
| Acrylamide/Sodium Acryloyldimethyl-taurate Copolymer (and) Isohexadecane (and) Polysorbate 80 | Simulgel 600 | 4.000 |
| Mica (and) Triethoxycaprylylsilane (and) Polyhydroxystearic Acid | GMS-11SP | 1.500 |

In yet another preferred embodiment, the current invention contemplates a formulation as follows in Table 3. It is understood the current invention is not limited to same and the below is for illustrative purposes.

TABLE 3

| CTFA Name | Trade Name | % (w/w) |
|---|---|---|
| Purified Water | Purified Water | 38.150 |
| Disodium EDTA | Versene NA | 0.100 |
| Niacinamide | Niacinamide | 0.500 |
| Urea | Urea | 5.000 |
| Xanthan Gum (and) *Acacia Senegal* Gum | Solagum AX | 1.000 |
| Glycerin USP | Glycerin | 1.000 |
| Ethoxydiglycol | Transcutol CG | 3.000 |
| Propylene Glycol | Propylene Glycol | 2.000 |
| Salicylic Acid (and) Allyl Methacrylates Copolymer | Polypore 450 SA | 0.900 |
| Glycolic Acid (and) Ammonium Glycolate | Glycolic 3.8 | 18.500 |
| Cetearyl Alcohol (and) Dicetyl Phosphate (and) Ceteth-10 Phosphate | Crodafos CES | 2.000 |
| PEG-100 Stearate (and) Glyceryl Stearate | Arlacel 165 | 3.000 |
| Caprylic/Capric Triglycerides | Neobee M5 | 5.000 |
| *Glycine Soja* (Soybean) Sterols | General 122 N PRL | 0.250 |
| Stearyl Alcohol | Stearyl Alcohol | 2.000 |
| Dimethicone | DC 200, 350cst | 3.000 |
| Ceramide NP (and) Ceramide AP (and) Ceramide EOP (and) Phytosphingosine (and) Cholesterol (and) Sodium Lauroyl Lactylate (and) Carbomer (and) Xanthan Gum | SK Influx | 2.000 |
| Saccharide Isomerate | Pentavitin | 4.000 |
| Water (and) Glycerin (and) *Avena Sativa* (Oat) Kernel Extract | DragoCalm | 2.000 |
| Phenoxyethanol (and) Ethylhexylglycerin | Euxyl PE 9010 | 1.000 |
| Acrylamide/Sodium Acryloyldimethyl-taurate Copolymer (and) Isohexadecane (and) Polysorbate 80 | Simulgel 600 | 4.000 |
| Mica (and) Triethoxycaprylylsilane (and) Polyhydroxystearic Acid | GMS-11SP | 1.500 |
| Biasabolol (and) *Zingiber Officinale* (Ginger) Root Extract | Symrelief 100 | 0.100 |

Formulation Summary

As mentioned above, mature skin is often prone to hyperkeratotic conditions due to depressed cell renewal. Knees and elbows are typical sites of HP, whereas Keratosis Pilaris (KP) usually affects the back of the arms and front of the legs. This condition can be treated with alpha hydroxy acids (AHAs) and/or keratolytic agents, such as Urea and Salicylic Acid. AHAs promote cell renewal by weakening the bonds between neighboring skin cells, thus allowing them to be more easily shed. On the other hand, keratolytic agents degrade keratin fibers that can accumulate and clog follicles. Utilizing a combination of Salicylic Acid, Glycolic Acid, and Urea will deliver an effective keratolytic effect, clear blockages, remove dead skin cells, and rid the skin of other cellular debris. To optimize the delivery and efficacy of these agents, the pH of the formulation will be acidic to maintain the acids in their "active" form and a penetration enhancer, Ethoxydiglycol, will be added. Lastly, the formulation may be rounded out by addition of barrier repair agents, anti-irritants, and humectants.

Keratolytic Agents

Salicylic Acid has long been recognized as an effective keratolytic agent and is used to treat such conditions as acne, dandruff, and seborrheic dermatitis. By penetrating into the follicle, Salicylic Acid encourages the sloughing of dead skin cells and other cellular debris and, ultimately, clears blockages. Further benefits of its exfoliating action are improvements in skin texture and hyperpigmentation. This formulation utilizes Polypore 450 SA, an extended release delivery system. Salicylic Acid is loaded into a polymer matrix to allow slow, extended release of the active. This slow release allows for long-lasting availability of the active, as well as less irritation. Urea also contributes keratolytic action via degradation of keratin fibers. In addition, it helps to increase water content in the skin.

Alpha-Hydroxy Acids

Glycolic Acid has been widely used to enhance cell turnover rates. As the smallest alpha-hydroxy acid, it is believed to have the best penetration into the skin. By weakening the lipid bonds between cells, glycolic acid allows dead skin cells to shed from the skin surface. In addition, glycolic acid is has also been used to help reduce the appearance of wrinkles, acne scars, hyperpigmentation, and hyperkeratotic skin conditions.

Barrier Repair/Humectancy

Improvements in skin moisture levels are achieved via a barrier effect to prevent water from escaping the skin. Symrepair, a synergistic blend of ceramide, free fatty acids, and phytosterol reconstitute and repair the skin barrier. Bisabolol, the active fraction of chamomile and a potent anti-inflammatory agent, is also a component of the blend and can help mitigate the irritating effects of hydroxy acids. Pure Soybean Sterols, a class of phytosterols, share a similar structure to that of cholesterol, an important component of the skin's lipid barrier. Aside from strengthening and repairing the skin barrier, phytosterols also have leucotriene inhibiting properties to deliver an anti-inflammatory effect. Soybean Sterols exhibit good penetration to provide emolliency and improve skin elasticity. Lastly, Saccharide Isomerate, engages in specializing binding with keratin fibers, allowing the carbohydrate to attract water while demonstrating high substantivity and resistance to wash-off. The combination of these barrier repair agents and humectants will help repair and reinforce the skin barrier, as well as offer a long-lasting moisturization effect.

Anti-Irritants

Hydroxy acids are typically associated with irritation, since their cell renewal and/or keratolytic effects occur under acidic conditions. The irritation and redness commonly associated with hydroxy acid use can be reduced by addition of anti-irritants. The previously mentioned Soybean Sterols and Bisabolol function to calm irritation and inflammation. In addition, another skin benefit of Saccharide Isomerate is its ability to help decrease the dryness and irritation associated with AHAs. SymCalmin, containing avenathramides, exhibits potent anti-histamine activity to calm itch and reduce redness. Lastly, Niacinamide (Vitamin B3) contributes anti-inflammatory and anti-oxidant activity, as well as improves barrier function via stimulation of ceramide production.

A number of implementations have been described herein. Nevertheless, it will be understood that various modifications may be made. Accordingly, other implementations are within the scope of the following claims. Changes may be made in the combinations, operations, and arrangements of the various parts, elements, and amounts described herein without departing from the spirit and scope of the invention.

We claim:

1. A method for treatment of dry skin, consisting of applying to the skin of a subject in need of such treatment a topical preparation comprising a pharmaceutically effective amount of Ethoxydiglycol, Allyl Methacrylates Crosspolymer, Salicylic Acid, Urea, Glycol Acid, Hexyldecanol, Bisabolol, Cetyl, Hydroxyproline Palmitate, Stearic Acid, *Brassica Campestris* Sterols, *Glycine Soja* Sterols, Saccharide Isomerate, Butylene Glycol, Pentylene Glycol, Hydroxyphenyl Propamidobenzoic Acid, and Niacinamide.

* * * * *